United States Patent [19]

Shepherd

[11] 4,325,953
[45] Apr. 20, 1982

[54] 4-ARYL-4-ARYLOXYPIPERIDINES

[75] Inventor: Robin G. Shepherd, Burnham, England

[73] Assignee: John Wyeth and Brother Limited, Maidenhead, England

[21] Appl. No.: 183,789

[22] Filed: Sep. 3, 1980

[30] Foreign Application Priority Data

Sep. 14, 1979 [GB] United Kingdom ............... 32046/79

[51] Int. Cl.³ .................. A61K 31/445; C07D 211/44
[52] U.S. Cl. ..................................... 424/250; 424/258; 424/267; 544/360; 544/408; 546/217; 546/193; 546/157
[58] Field of Search ............... 544/408, 360; 546/217, 546/157, 193; 424/250, 258, 267

[56] References Cited

U.S. PATENT DOCUMENTS 2,498,435  2/1950  Lee et al. ........................... 546/217
4,031,221  6/1977  Helsley et al. ..................... 424/267
4,116,963  9/1978  Adelstein .......................... 424/267

FOREIGN PATENT DOCUMENTS 42-1181  1/1967  Japan ................................. 546/157

OTHER PUBLICATIONS

Rajsner, et al., "Chemical Abstracts", vol. 59, (1963), 13935–13936d.

*Primary Examiner*—Anton H. Sutto
*Attorney, Agent, or Firm*—George Tarnowski

[57] ABSTRACT

4-Aryl-4-aryloxypiperidines of the general formula (I)

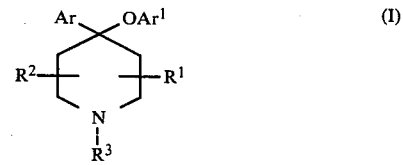

and their pharmaceutically acceptable acid addition salts, wherein $R^1$ and $R^2$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups and $Ar^1$ is a phenyl radical optionally substituted by one or more cyano, methylsulphinyl, methylsulphonyl, lower alkoxy, trifluoromethyl, lower alkyl, lower alkenyl, halogen, nitro, amino or acylamino groups or an aromatic heterocyclic mono- or di-cyclic radical, exhibit activity on the central nervous system, e.g. as antidepressants.

20 Claims, No Drawings

4-ARYL-4-ARYLOXYPIPERIDINES

This invention relates to 4-aryl-4-aryloxypiperidines, to a process for preparing them, to their use and to pharmaceutical preparations containing them.

The present invention provides 4-aryl-4-aryloxypiperidines of the general formula (I)

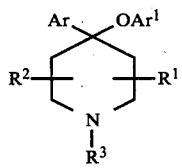

and their pharmaceutically acceptable acid addition salts, wherein $R^1$ and $R^2$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups and $Ar^1$ is a phenyl radical optionally substituted by one or more cyano, methylsulphinyl, methylsulphonyl, lower alkoxy, trifluoromethyl, lower alkyl, lower alkenyl, halogen, nitro, amino or acylamino groups or an aromatic heterocyclic mono- or di-cyclic radical such as 2- or 4-pyridyl, 2-pyrazinyl, 2-quinolinyl, 2-benzimidazyl, 2-thienyl and 2-thiazolyl.

The invention also provides a process for preparing a compound of general formula (I) or a pharmaceutically acceptable acid addition salt thereof, which comprises reacting an anion of an alcohol of general formula (II)

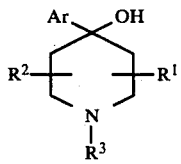

(where Ar, $R^1$, $R^2$ and $R^3$, are as defined above) with a halo compound of general formula (III)

$XAr^1$ (III)

[where X is fluorine and $Ar^1$ is an optionally substituted phenyl radical as defined above other than a lower alkoxy, amino or acylamino substituted phenyl or X is fluorine, chlorine or bromine (preferably fluorine) and $Ar^1$ is nitrophenyl or a heterocyclic radical as defined above]. The reaction may be carried out in a dipolar aprotic solvent. Examples of dipolar aprotic solvents include dimethylsulphoxide, dimethylformamide, hexamethylphosphoric triamide and sulpholane. Preferably the solvent is dimethylsulphoxide. The anion of the alcohol of general formula (II) is preferably formed by reacting the alcohol with potassium or sodium hydride or an alkyl or phenyl lithium (e.g. butyl lithium) in a compatible dipolar aprotic solvent. Preferably the alcohol is reacted with sodium hydride.

The process of the invention can be carried out at convenient temperatures e.g. 0° to 100° C. (for example room temperature); there is generally no need to use reflux temperatures. Good yields of products are generally obtained in relatively short reaction times.

If in the process described above the compound of the general formula (I) is obtained as an acid addition salt, such as a pharmaceutically acceptable acid addition salt or an acid addition salt such as an oxalate, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

Once a compound of general formula (I) is obtained, if desired it can be converted into another 4-aryl-4-aryloxypiperidine by known methods. For example a compound of formula (I) in which $Ar^1$ is a nitrophenyl group can be reduced to a compound in which $Ar^1$ is an aminophenyl. The aminophenyl substituent can be acylated to an acylaminophenyl substituent or may be diazotised and converted by standard procedures to a halophenyl, alkoxyphenyl or unsubstituted phenyl substituent. Compounds in which $R^3$ is hydrogen can be alkylated to give compounds in which $R^3$ is lower alkyl.

The compounds of general formula (I) may possess one or more asymmetric carbon atoms, depending upon the particular substituents. The compounds can therefore exist in various stereochemical forms. It will be realised that if the starting material of formula (II) is a mixture of isomers which may be separated, if required, by standard procedures. If the starting material is a single isomer then the product will also be a single isomer.

The term "lower" as used herein means that the radical referred to contains 1 to 6 carbon atoms. The radical preferably contains 1 to 4 carbon atoms. Examples of lower alkyl radicals include methyl, ethyl, propyl and butyl. Examples of lower alkoxy radicals include methoxy, ethoxy, propoxy and butoxy. Examples of lower alkenyl radicals include allyl and methallyl. When $R^1$, $R^2$ and/or $R^3$ represent lower alkyl, the lower alkyl group is preferably a straight chain radical such as methyl, ethyl, n-propyl or n-butyl although $R^3$ may also be, for example, a branched chain lower alkyl group such as isopropyl. When Ar or $Ar^1$ is substituted by halogen, the halogen may be fluoro, chloro, bromo or iodo. When $Ar^1$ is substituted by acylamino the substituent can be, for example, acetamido.

The compounds of general formula (I) and their pharmaceutically acceptable acid addition salts, possess pharmacological activity. In particular the compounds exhibit activity on the central nervous system, e.g. as antidepressants, as indicated by one or more of the standard test procedures such as the reserpine hypothermia procedure based upon B. M. Askew, Life Sciences (1963), 1, 725–730, the inhibition of noradrenaline or 5-hydroxytryptamine uptake in rat brain slices, the potentiation and prolongation of the effects of amphetamine and the modification of the effects of p-chloroamphetamine. For example, 2-(1-methyl-4-phenyl-4-piperidinyloxy)pyridine, a representative compound of the invention, in the reserpine hypothermia procedure produced a rise in rectal temperature compared to the control of 8.4° C. at 10 mg/kg and 10.2° C. at 30 mg/kg. Some of the compounds also possess analgesic activity.

The invention further provides a method of treating, depression which comprises administering to a warm blooded mammal, particularly a human, a therapeutically effective amount of a compound of the invention. The invention also provides a pharmaceutical composition comprising a compound of the invention in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form.

The following Examples illustrate the invention:

EXAMPLE 1

4-(4-Nitrophenoxy)-4-phenylpiperidine

A mixture of 4-phenyl-4-piperidinol (3.55 g) dimethylsulphoxide (DMSO) (50 ml) and sodium hydride (960 mg of 50% dispersion in oil 20 mM) was stirred for 1 hour and treated with 4-fluoronitrobenzene (B 2.82 g) (exothermic) and the reaction mixture stirred overnight. The reaction was poured onto a mixture of 2 N hydrochloric acid (100 ml) and ether (400 ml), the resulting solid removed by filtration and washed well with ether. Recrystallisation from IPA gave the title compound as the hydrochloride (1 g) m.p. 203°–5° C.

Found: C, 60.8; H, 5.8; N, 8.05%. $C_{17}H_{18}N_2O_3$ requires: C, 61.0; H, 5.7; N, 8.4%.

EXAMPLE 2

2-(1-Methyl-4-phenyl-4-piperidinyloxy)pyridine

A solution of 1-methyl-4-phenyl-4-piperidinol (prepared by reaction of 1-methyl-4-piperidone with phenyl lithium; 3.83 g, 20 mM) in dry DMSO (50 ml) was treated with sodium hydride (960 mg of 50% dispersion in oil, 20 mM), stirred for 1 hour then treated with 2-fluoro-pyridine (1.94 g, 20 mM). After 48 hours the reaction was poured on to water (200 ml) and extracted with ether (3×200 ml). The organic extract was washed with brine, dried and the solvent removed under reduced pressure. Recrystallisation of the residue from cyclohexane gave the title compound (2.0 g,) m.p. 95°–6° C.

Found: C, 76.4; H, 7.6; N, 10.3%. $C_{17}H_{20}N_2O$ requires: C, 76.1; H, 7.5; N, 10.4%.

EXAMPLE 3

1-Methyl-4-(2-nitrophenoxy)-4-phenylpiperidine

A solution of 1-methyl-4-phenyl-4-piperidinol (7.65 g, 40 mM) in dry DMSO (100 ml) was treated with sodium hydride (2.0 g of 50% dispersion in oil 42 mM), the mixture stirred for 1 hour and then treated with 2-fluoronitrobenzene (5.65 g, 40 mM). After 24 hours the reaction mixture was poured in to water (500 ml) and extracted with ether (2×500 ml). The organic extract was washed with brine, dried and the solvents removed under reduced pressure. Recrystallisation of the residue from cyclohexane gave the title compound (4.1 g) m.p. 80°–2° C.

Found: C, 69.5; H, 6.5; N, 8.6%. $C_{18}H_{20}N_2O_3$ requires: C, 69.2, H, 6.5; N, 9.0%.

EXAMPLE 4

2-(1-Methyl-4-phenyl-4-piperidinyloxy)pyrazine

A solution of 1-methyl-4-phenyl-B 4-piperidinol (7.65 g, 40 mM), in DMSO (100 ml) was treated with 50% sodium hydride dispersion (2.0 g, 40 mM) and the mixture warmed to 80° until a clear solution was obtained. After cooling to room temperature a solution of 2-chloropyrazine (5.6 g, 40 mM) in DMSO (10 ml) was added. After 48 hours the reaction mixture was poured on to water (400 ml), extracted with ether (3×250 ml), the organic phase dried and the solvents removed under reduced pressure. Recrystallisation of the residue from cyclohexane gave recovered 1-methyl-4-phenyl-4-piperidinol (2 g). Chromatography of the mother liquors on Grade III silica using 3% methanol in chloroform as eluant, evaporation of the appropriate fractions and recrystallisation from pentane gave the title compound (1.2 g) m.p. 115°–6° C.

Found: C, 71.0; H, 7.35; N, 15.8%. $C_{16}H_{19}N_3O$ requires: C, 71.3; H, 7.1; N, 15.6%.

EXAMPLE 5

1-Benzyl-4-(4-nitrophenoxy)-4-phenylpiperidine

A solution of 1-benzyl-4-hydroxy-4-phenylpiperidine (5.35 g, 20 mM) in dry DMSO (50 ml) was treated with a 50% sodium hydride dispersion (960 mg, 20 mM) followed by 4-fluoronitrobenzene (2.82 g, 20 mM). After 24 hours the reaction mixture was partitioned between water (200 ml) and ether (200 ml). The aqueous layer was extracted with ether (2×200 ml) and the combined organic layers washed with water (200 ml). The organic phase was dried and the solvent removed under reduced pressure. Recrystallisation of the residue from IPA gave the title compound (3.5 g) m.p. 135°–7° C.

Found: C, 74.4; H, 6.6; N, 6.9%. $C_{24}H_{24}N_2O_3$ requires: C, 74.2; H, 6.2; N, 7.2%.

EXAMPLE 6

4-(4-Aminophenoxy)-4-phenyl-1-benzylpiperidine

A solution of 1-benzyl-4-(4-nitrophenoxy)-4-phenylpiperidine (1.95 g, 5 mM), in methanol (100 ml) was hydrogenated over 5% Pd/C at atmospheric pressure and room temperature. After the theoretical uptake of hydrogen had occurred (about 2 hours), the catalyst was removed by filtration and the solvents removed under reduced pressure. Recrystallisation of the residue from IPA (twice) gave the title compound (400 mg), m.p. 124°–6° C.

Found: C, 80.2; H, 7.7; N, 7.7%. $C_{24}H_{26}N_2O$ requires: C, 80.4; H, 7.3; N, 7.8%.

EXAMPLE 7

2-(1-Methyl-4-phenyl-4-piperidinyloxy)quinoline

A solution of 1-methyl-4-phenyl-4-piperidinol (7.65 g, 40 mM) in DMSO (50 ml) was treated with 50% sodium hydride dispersion (2 g, 40 mM) and warmed to 80° until a homogenous solution was obtained. After cooling to room temperature, the mixture was treated with a solution of 2-chloroquinoline (6.55 g, 40 mM) in DMSO (10 ml). After 24 hours the mixture was poured on to water (250 ml) and extracted with toluene (3×250 ml). After drying and evaporation of the solvents, the residue crystallised from cyclohexane to give recovered 1-methyl-4-phenyl-4-piperidinol (2.7 g). Chromatography of the mother liquors on Grade III silica, using 3% methanol in chloroform as eluant gave the title compound (3 g) contaminated with a small quantity of 2-quinolone which was removed by crystallisation from cyclohexane. Recrystallisation of the mother liquors from pentane gave the title compound (1.2 g) m.p. 80°–1° C.

Found: C, 79.3; H, 7.2; N, 8.4%. $C_{21}H_{22}N_2O$ requires: C, 79.2; H, 7.0; N, 8.8%.

EXAMPLE 8

2-(4-Phenyl-1-benzyl-4-piperidyloxy)pyrazine

A solution of 4-phenyl-1-phenylmethyl-4-piperidinol (5.35 g, 20 mM) in DMSO (50 ml) was treated with sodium hydride (960 mg of a 50% dispersion, 20 mM) followed by chloropyrazine (2.29 g, 20 mM); the reaction was stirred for 24 hours and then poured on to water (200 ml). The aqueous layer was extracted with ether (3×100 ml), the combined organic phases washed with water (100 ml) and dried. Removal of the solvents under reduced pressure followed by recrystallisation gave the title compound (1.3 g), m.p. 107°–8° C.

Found: C, 76.9; H, 7.0; N, 12.3%. $C_{22}H_{23}N_3O$ requires: C, 76.5; H, 6.7; N, 12.2%.

EXAMPLE 9

2-(4-Phenyl-4-piperidinyloxy)pyridine

A solution of 4-phenyl-4-piperidinol (7.1 g, 40 mM) in dry DMSO (50 ml) was treated with a 50% sodium hydride dispersion (2.0 g, 40 mM) and the mixture warmed to 80°, until a clear solution was obtained. The solution was cooled to room temperature and treated with a solution of 2-fluoropyridine (3.9 g, 40 mM) in DMSO (10 ml). After 24 hours the reaction mixture was poured onto water (250 ml) and extracted with toluene (3×250 ml). After washing with brine, the organic phase was dried (MgSO₄) and the solvents removed under reduced pressure. Recrystallisation from IPE gave the title compound (3.5 g) contaminated with traces of 4-phenyl-4-piperidinol. Fractional crystallisation from cyclohexane gave the title compound analytically pure and chromatographically homogenous (600 mg) m.p. 86°–7°.

Found: C, 75.7; H, 7.1; N, 10.95%. $C_{16}H_{18}N_2O$ requires: C, 75.6; H, 7.1; N, 11.0%.

EXAMPLE 10

1-Methyl-4-(4-nitrophenoxy)-4-phenylpiperidine

A solution of 1-methyl-4-phenyl-4-piperidinol (7.65 g, 40 mM) in dry DMSO (100 ml) was treated with sodium hydride (2.0 g of a 50% dispersion in oil, 42 mM). The reaction mixture was stirred for 1 hour then treated with 4-fluoronitrobenzene (5.65 g, 40 mM). After 24 hours the reaction mixture was poured on to water (500 ml) and extracted with ether (4×500 ml). The organic extracts were washed with brine, dried and the solvents removed under reduced pressure. Recrystallisation of the residue from IPA gave the title compound (6.1 g) m.p. 136°–8°.

Found: C, 69.5; H, 6.2; N, 8.6%. $C_{18}H_{20}N_2O_3$ requires: C, 69.2; H, 6.5; N, 9.0%.

EXAMPLE 11

2-(4-Phenyl-4-piperidinyloxy)pyrazine

A mixture of 4-phenyl-4-piperidinol (7.1 g, 40 mM), DMSO (50 ml) and sodium hydride (2 g of a 50% dispersion in oil) was heated at 80° until homogenous, cooled to room temperature and treated with chloropyrazine (4.6 g, 40 mM) in DMSO (10 ml). After 24 hours the reaction mixture was poured on to water (250 ml) and extracted with toluene (2×250 ml). The combined organic phases were washed with brine, dried and the solvents removed under reduced pressure. Sublimation of the residue at 0.1 mm Hg (bath temp. 100°) gave the title compound (400 mg) m.p. 107°–8°.

Found: C, 70.25; H, 7.0; N, 16.1%. $C_{15}H_{17}N_3O$ requires: C, 70.6; H, 6.7; N, 16.5%.

EXAMPLE 12

1-Methyl-4-phenyl-4-(4-trifluoromethylphenoxy)piperidine

A mixture of 4-hydroxy-1-methyl-4-phenylpiperidine (4.6 g), DMSO (50 ml) and sodium hydride (1.2 g of a 50% dispersion in oil) was heated at 80° until homogenous, cooled to room temperature and treated with 4-fluorobenzotrifluoride (4 g) in DMSO (5 ml). After 24 hours the reaction mixture was poured on to cold water (250 ml) and extracted with ether (2×250 ml). The combined organic phases were washed with brine, dried and heated with excess etherial hydrogen chloride. Removal of the resultant precipitate by filtration and drying in vacuo gave the title compound as the hydrochloride three quarter hydrate (3.3 g), m.p. 227°.

Found: C, 60.7; H, 5.8; N, 3.8%. $C_{19}H_{20}F_3NO.HCl.3/4H_2O$ requires: C, 60.6; H, 5.8; N, 3.7%.

EXAMPLE 13

4-(4-Aminophenoxy)-1-methyl-4-phenylpiperidine

A solution of 1-methyl-4-(4-nitrophenoxy)-4-phenylpiperidine (4.4 g, 14.1 mM) in methanol (250 ml) was hydrogenated at 1 atmosphere and ambient temperature over 5% palladium on charcoal (500 mg) until the theoretical uptake of hydrogen had occurred (about 2 hours). The catalyst was removed by filtration and the solvent evaporated under reduced pressure. Recrystallisation of the residue from IPA gave the title compound (2 g) m.p. 174°–5°.

Found: C, 76.6; H, 8.0; N, 9.8%. $C_{18}H_{22}N_2O$ requires: C, 76.6; H, 7.8; N, 9.9%.

EXAMPLE 14

4-Phenyl-4-(4-trifluoromethylphenoxy)piperidine

A mixture of 4-phenyl-4-piperidinol (7.1 g, 40 mM), DMSO (50 ml) and sodium hydride (2 g of a 50% dispersion in oil) was heated at 80° until homogenous, cooled to ambient temperature and treated with 4-fluorobenzotrifluoride (6.6 g, 40 mM) in DMSO (10 ml). After 24 hours the reaction mixture was poured on to cold water (250 ml) and extracted with ether (2×250 ml). The combined organic layers were washed with brine, dried and the solvent removed under reduced pressure. The residue was triturated with cyclohexane, filtered and the mother liquors evaporated and the residue triturated with pentane. Sublimation of the resulting crystals at 0.1 mm Hg (bath temp. 100°) gave the title compound (1.5 g), m.p. 104°–5°.

Found: C, 67.2; H, 5.1, N, 4.2%. $C_{18}H_{18}F_3NO$ requires: C, 67.3; H, 5.6; N, 4.4%.

EXAMPLE 15

4-(2-Aminophenoxy)-1-methyl-4-phenylpiperidine

A solution of 1-methyl-4-(2-nitrophenoxy)-4-phenylpiperidine (6.4 g) in methanol (200 ml) was hydrogenated at atmospheric pressure and ambient temperature until the theoretical uptake of hydrogen had occurred (about 2 hours). The catalyst was removed by filtration, the solvent removed under reduced pressure and the residue recrystallised twice from IPE to give the title compound (4.5 g) m.p. 129°–30°.

Found: 76.8; H, 7.8; N, 9.7%. $C_{18}H_{22}N_2O$ requires: C, 76.6; H, 7.9; N, 9.9%.

EXAMPLE 16

1-Methyl-4-phenoxy-4-phenylpiperidine

A solution of 4-(4-aminophenoxy)-1-methyl-4-phenylpiperidine (2.82 g, 10 mM), in THF (75 ml) was added over 2 hours to a refluxing solution of amyl nitrite (2.7 ml, 20 mM) in THF (30 ml). After 5 hours at reflux amyl nitrite (1.5 ml) was added and the mixture maintained at reflux for 24 hours. The solvent was removed under reduced pressure and the residue partitioned between 2 N hydrochloric acid (50 ml) and ether (50 ml). The aqueous phase was basified (pH9) and extracted with ether (2×100 ml). The organic phase was dried and the solvents removed under reduced pressure. Sublimation of the residue at 1.0 mbar pressure (bath temp. 100°) gave the title compound (700 mg), m.p. 103°–4°.

Found: C, 80.7; H, 8.2; N, 5.2%. $C_{18}H_{21}NO$ requires: C, 80.9; H, 7.9; N, 5.2%.

EXAMPLE 17

4-(4-Acetamidophenoxy)-1-methyl-4-phenylpiperidine

A solution of 1-methyl-4-phenoxy-4-phenylpiperidine (2.8 g) in dichloromethane (25 ml) was treated with acetic anhydride (1.5 ml) (exothermic). After 2 h the mixture was extracted with saturated aqueous sodium bicarbonate solution followed by brine. The organic phase was dried and the solvent removed under reduced pressure. Recrystallisation of the residue from IPE gave the title compound (1.4 g) as the quarter hydrate m.p.: 146°–8°.

Found: C, 73.1; H, 7.4; N, 8.4%. $C_{20}H_{24}N_2\frac{1}{4}H_2O$ requires: C, 73.0; H, 7.5; N, 8.5%.

EXAMPLE 18

1-Ethyl-4-(4-nitrophenoxy)-4-phenylpiperidine

A mixture of 4-(p-nitrophenoxy)-4-phenylpiperidine oxalate (3.3 g), 2,2,6,6-tetramethylpiperidine (4.3 ml, 25 mM), ethyl iodide (0.69 ml, 8.5 mM) and acetonitrile (100 ml) was stirred for 24 h at ambient temperature. The resulting precipitate was removed by filtration and washed with acetonitrile (3×10 ml). The combined filtrate and washings were evaporated under reduced pressure and the residue partitioned between saturated aqueous sodium carbonate (50 ml) and ether (200 ml). The ether layer was dried, the solvent removed under reduced pressure and the residue dissolved in ethyl acetate (100 ml). Treatment of the ethyl acetate solution with an excess of a solution of oxalic acid dihydrate in ethyl acetate followed by removal of the resulting precipitate by filtration and air drying gave the title compound as the oxalate hemihydrate (1.4 g) m.p.: 188°–190° (decomp).

Found: C, 59.1; H, 5.9; N, 6.4%. $C_{19}H_{22}N_2O_3.C_2H_2O_4\frac{1}{2}H_2O$ requires: C, 59.3; H, 5.9; N, 6.6%.

EXAMPLE 19

1-Methyl-4-(4-methylphenyl)-4-(4-nitrophenoxy)piperidine

A mixture of 1-methyl-4-(4-methylphenyl)-4-piperidinol ((5.2 g), (prepared by reaction of 1-methyl-4-piperidone with p-methylphenyl magnesium bromide), sodium hydride (1.25 g) and DMSO (50 ml) was heated at 80° until homogenous, cooled to ambient temperature and treated with a solution of 4-fluoronitrobenzene (3.54 g) in DMSO (10 ml) (with cooling). After 1 h the reaction mixture was poured on to water (250 ml) and extracted with ether (2×250 ml). The organic phase was washed with brine, dried and the solvent removed under reduced pressure. The residue was chromatographed on Grade 3 silica using 2% methanol in chloroform as eluant. Evaporation of the appropriate fractions gave an oil (3.9 g) which was dissolved in ethyl acetate and treated with an excess of oxalic acid in ethyl acetate. Removal of the resulting precipitate by filtration followed by washing with ethyl acetate and air drying gave the title compound as the oxalate (4 g) m.p: 167°–9°(d).

Found: C, 61.0; H, 6.3; N, 6.4%. $C_{19}H_{22}N_2O_3 \cdot C_2H_2O_4$ requires: C, 60.6; H, 5.8; N, 6.7%.

EXAMPLE 20

4-(4-Chlorophenyl)-4-(4-nitrophenoxy)piperidine

A mixture of 4-(4-chlorophenyl)-4-piperidinol (7.1 g), sodium hydride (2 g of 50% dispersion, 40 mM) and DMSO (100 ml) was heated at 80° until homogenous, cooled to room temperature and treated with a solution of 4-fluoronitrobenzene (5.65 g) in DMSO (10 ml) (with cooling). After 1 h, the mixture was poured on to water (500 ml) and extracted with toluene (2×250 ml). The organic layer was washed with brine, dried and the solvent removed under pressure. The residue was dissolved in ethyl acetate and treated with an excess of a solution of oxalic acid dihydrate in ethyl acetate. Removal of the resulting precipitate by filtration, washing with ethyl acetate and drying in vacuo gave the title compound as the oxalate hemihydrate (3.3 g) m.p. 195°–7°(d)

Found: C, 52.6; H, 4.6; N, 6.0%. $C_{17}H_{17}ClN_2O_3 \cdot C_2H_2O_4 \cdot \frac{1}{2}H_2O$ requires: C, 52.8; H, 4.7; N, 6.5%.

EXAMPLE 21

4-(4-Chlorophenyl)-1-methyl-4-(4-nitrophenoxy)piperidine

A mixture of 4-(4-chlorophenyl)-1-methyl-4-piperidinol (4.5 g, 20 mM), sodium hydride (960 mg of 50% dispersion, 20 mM) and DMSO (50 ml) was heated at 80° until homogenous, cooled to ambient temperature and treated with 4-fluoronitrobenzene (2.8 g, 20 mM). After 2 h the reaction mixture was poured on to ice/water and extracted with ethyl acetate (2×250 ml). The organic phase was washed with brine, dried and the solvent removed under reduced pressure. The residue was redissolved in ethyl acetate (100 ml) and treated with a solution of oxalic acid dihydrate (2.5 g) in ethyl acetate (100 ml). The resulting crystals were removed by filtration and air dried to give the title compound as the oxalate hemihydrate (4 g) m.p. 201°–3° decomp.

Found: C, 54.1; H, 5.0; N, 5%. $C_{18}H_{19}ClN_2O_3 \cdot C_2H_2O_4 \cdot \frac{1}{2}H_2O$ requires: C, 53.9; H, 5.0; N, 6.3%.

I claim:

1. A compound selected from the group consisting of a 4-aryl-4-aryloxypiperidine of the formula (I)

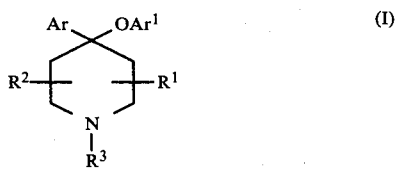

and a pharmaceutically acceptable acid addition salt thereof, wherein $R^1$ and $R^2$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups and $Ar^1$ is a phenyl radical optionally substituted by one or more cyano, methylsulphinyl, methylsulphonyl, lower alkoxy, trifluoromethyl, lower alkyl, lower alkenyl, halogen, nitro, amino or acylamino groups or is a 2- or 4-pyridyl, 2-pyrazinyl or 2-quinolinyl radical with the proviso that when $R^3$ is hydrogen or benzyl and Ar is phenyl, $Ar^1$ is other than phenyl or phenyl substituted by one or more lower alkoxy, trifluoromethyl, lower alkyl, halogen or nitro groups.

2. A pharmaceutical composition having antidepressant activity which comprises a compound selected from the group consisting of a 4-aryl-4-aryloxypiperidine of the formula (I)

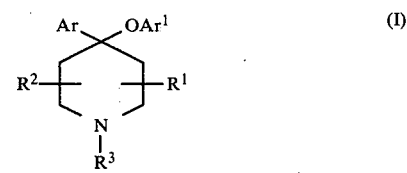

and a pharmaceutically acceptable acid addition salt thereof, wherein $R^1$ and $R^2$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups and $Ar^1$ is a phenyl radical optionally substituted by one or more cyano, methylsulphinyl, methylsulphonyl, lower alkoxy, trifluoromethyl, lower alkyl, lower alkenyl, halogen, nitro, amino or acylamino groups or is a 2- or 4-pyridyl, 2-pyrazinyl or 2-quinolinyl, radical in association with a pharmaceutically acceptable carrier.

3. A compound selected from the group consisting of a 4-aryl-4-aryloxypiperidine of the formula (I)

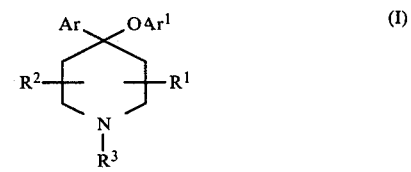

and a pharmaceutically acceptable acid addition salt thereof, wherein $R^1$ and $R^2$ are hydrogen or lower alkyl, $R^3$ is hydrogen, lower alkyl or benzyl, Ar is phenyl optionally substituted by one or more halogen, trifluoromethyl, lower alkyl, lower alkoxy, nitro or amino groups and $Ar^1$ is a phenyl radical optionally substituted by one or more cyano, methylsulphinyl, methylsulphonyl, lower alkoxy, trifluoromethyl, lower alkyl, lower alkenyl, halogen, nitro, amino or acylamino groups or is a 2- or 4-pyridyl, 2-pyrazinyl or 2-quinolinyl, radical.

4. A compound as claimed in claim 3 which is 2-(1-methyl-4-phenyl-4-piperidinyloxy)pyridine or a pharmaceutically acceptable acid addition salt thereof.

5. A compound as claimed in claim 3 which is 1-methyl-4-(2-nitrophenoxy)-4-phenylpiperidine or a pharmaceutically acceptable acid addition salt thereof.

6. A compound as claimed in claim 3 which is 2-(1-methyl-4-phenyl-4-piperidinyloxy)pyrazine or a pharmaceutically acceptable acid addition salt thereof.

7. A compound as claimed in claim 3 which is 4-(4-aminophenoxy)-4-phenyl-1-benzylpiperidine or a pharmaceutically acceptable acid addition salt thereof.

8. A compound as claimed in claim 3 which is 2-(1-methyl-4-phenyl-4-piperidinyloxy)quinoline or a pharmaceutically acceptable acid addition salt thereof.

9. A compound as claimed in claim 3 which is 2-(4-phenyl-1-benzyl-4-piperidyloxy) pyrazine or a pharmaceutically acceptable acid addition salt thereof.

10. A compound as claimed in claim 3 which is 2-(4-phenyl-4-piperidinyloxy)pyridine or a pharmaceutically acceptable acid addition salt thereof.

11. A compound as claimed in claim 3 which is 1-methyl-4-(4-nitrophenoxy)-4-phenylpiperidine or a pharmaceutically acceptable acid addition salt thereof.

12. A compound as claimed in claim 3 which is 2-(4-phenyl-4-piperidinyloxy)pyrazine or a pharmaceutically acceptable acid addition salt thereof.

13. A compound as claim 3 which is 1-methyl-4-phenyl-4-(4-trifluoromethylphenoxy) piperidine or a pharmaceutically acceptable acid addition salt thereof.

14. A compound as claimed in claim 3 which is 4-(4-aminophenoxy)-1-methyl-4-phenylpiperidine or a pharmaceutically acceptable acid addition salt thereof.

15. A compound as claimed in claim 3 which is 4-(2-aminophenoxy)-1-methyl-4-phenylpiperidine or a pharmaceutically acceptable acid addition salt thereof.

16. A compound as claimed in claim 3 which is 1-methyl-4-phenoxy-4-phenylpiperidine or a pharmaceutically acceptable acid addition salt thereof.

17. A compound as claimed in claim 3 which is 4-(4-acetamidophenoxy)-1-methyl-4-phenylpiperidine or a pharmaceutically acceptable acid addition salt thereof.

18. A compound as claimed in claim 3 which is 1-ethyl-4-(4-nitrophenoxy)-4-phenylpiperidine or a pharmaceutically acceptable acid addition salt thereof.

19. A compound as claimed in claim 3 which is 1-methyl-4-(4-methylphenyl)-4-(4-nitrophenoxy) piperidine or a pharmaceutically acceptable acid addition salt thereof.

20. A compound as claimed in claim 3 which is 4-(4-chlorophenyl)-4-(4-nitrophenoxy)piperidine or a pharmaceutically acceptable acid addition salt thereof.

* * * * *